United States Patent [19]

Iglesia et al.

[11] Patent Number: 4,738,948

[45] Date of Patent: Apr. 19, 1988

[54] COBALT-RUTHENIUM CATALYSTS FOR FISCHER-TROPSCH SYNTHESIS AND PROCESS FOR THEIR PREPARATION

[75] Inventors: Enrique Iglesia, Clinton; Stuart L. Soled, Pittstown; Rocco A. Fiato, Basking Ridge, all of N.J.

[73] Assignee: Exxon Research and Engineering Company, Florham Park, N.J.

[21] Appl. No.: 881,347

[22] Filed: Jul. 2, 1986

[51] Int. Cl.$^4$ .............................................. B01J 23/89
[52] U.S. Cl. ..................................... 502/326; 518/715
[58] Field of Search ......................... 502/326; 518/715

[56] References Cited

U.S. PATENT DOCUMENTS

| | | | |
|---|---|---|---|
| 4,042,614 | 8/1977 | Vannice et al. | 502/242 X |
| 4,088,671 | 5/1978 | Kobylinski | 518/715 |
| 4,585,798 | 4/1986 | Beuther et al. | 518/715 |
| 4,595,703 | 6/1986 | Payne et al. | 518/715 |

*Primary Examiner*—W. J. Shine
*Attorney, Agent, or Firm*—Jay Simon

[57] ABSTRACT

A hydrogen regenerable hydrocarbon synthesis catalyst useful for preparing higher hydrocarbons from synthesis gas is prepared by depositing cobalt and ruthenium on a refractory carrier and oxidizing and reducing the catalytic metals to form a catalyst in which the cobalt and ruthenium are in intimate contact.

10 Claims, 4 Drawing Sheets

COBALT-RUTHENIUM CATALYSTS FOR FISCHER-TROPSCH SYNTHESIS AND PROCESS FOR THEIR PREPARATION

BACKGROUND OF THE INVENTION

1. Field of the Invention

This invention relates to an improved catalyst for producing hydrocarbons from synthesis gas, hydrogen and carbon monoxide, and to improvements in the hydrocarbon synthesis process. Specifically, this invention relates to a catalyst comprising cobalt and ruthenium in catalytically active amounts on a titania support and a process for utilizing the catalyst that allows on-stream regeneration and cyclical operation without having to remove the catalyst from the hydrocarbon synthesis reactor.

2. The Prior Art

Methane is available in large quantities in many areas of the world. Some methane is generated from refinery applications while large amounts of methane, as the principal constituent of natural gas, are found in deposits in various areas. Methane can be used as a gas, for example, for heating purposes, and can be transported by pipeline or as a liquefied gas over long distances. Where use of the methane as a gas is not economic or the transportation of methane requires traversing oceans, the methane can be converted to a liquid which is more easily transported and may have significantly higher value than methane gas.

Conversion of methane is normally carried out in a two-step procedure involving reforming the methane to produce hydrogen and carbon monoxide, synthesis gas, and converting the synthesis gas to higher hydrocarbons, $C_{5}+$, in a Fischer-Tropsch type reaction. Both steps of the process are well known and can be readily illustrated: the first step by U.S. Pat. Nos. 1,711,036, 1,960,912 and 3,138,438; the second step by U.S. Pat. Nos. 4,477,595, 4,542,122, and 4,088,671.

This invention is concerned with the second step, the well known Fischer-Tropsch type reaction which will be referred to hereinafter as hydrocarbon synthesis.

This invention is primarily concerned with cobalt and ruthenium catalysts for hydrocarbon synthesis and both of these metals have been disclosed as being useful in such reactions, either alone, jointly, or with other materials. What has not been disclosed in the art is the combination of steps required to produce a composition that is novel and has superior catalytic properties to other cobalt, ruthenium, or cobalt-ruthenium catalysts. These properties include: improved CO conversion, improved volumetric productivity, enhanced selectivity to $C_{5}+$ and lower $CH_4$ and the ability to regenerate the catalyst at relatively low temperatures without removing it from the reactor.

U.S. Pat. No. 4,477,595 discloses ruthenium on titania as a hydrocarbon synthesis catalyst for the production of $C_5$ to $C_{40}$ hydrocarbons with a majority of paraffins in the $C_5$ to $C_{20}$ range. U.S. Pat. No. 4,542,122 discloses a cobalt or cobalt-thoria on titania having a preferred ratio of rutile to anatase, as a hydrocarbon synthesis catalyst. U.S. Pat. No. 4,088,671 discloses a cobalt-ruthenium catalyst where the support can be titania but preferably is alumina for economic reasons. U.S. Pat. No. 4,413,064 discloses an alumina supported catalyst having cobalt, ruthenium and a Group IIIA or Group IVB metal oxide, e.g., thoria. European Patent No. 142,887 discloses a silica supported cobalt catalyst together with zirconium, titanium, ruthenium and/or chromium.

SUMMARY OF THE INVENTION

The invention resides in the preparation of a novel catalyst and the use of that catalyst in hydrocarbon synthesis reactions. The catalyst is comprised of cobalt and ruthenium, in intimate association, deposited on a titania support. Evidence suggests that atoms of cobalt and ruthenium are present in the same crystallite and that this intimate association of the metals provides the advantages mentioned hereinbelow.

The catalyst, when prepared as described herein, is an excellent hydrocarbon synthesis catalyst and may be used in hydrocarbon synthesis reactions as other known catalysts are used, for example, as pellets loaded in tubes through which synthesis gas is passed and converted into higher hydrocarbons. The advantages of employing the particular cobalt-ruthenium catalyst of this invention in hydrocarbon synthesis are: lower methane yields and increased $C_{5}+$ yields relative to a cobalt catalyst or a cobalt-ruthenium catalyst that has not been oxidized and re-reduced in accordance with this disclosure, greater cobalt time yields (that is, greater conversion of CO and $H_2$ per gram atom of cobalt per unit of time—a measure of catalyst activity) and the ability to regenerate the catalyst, in situ, under low temperature flowing hydrogen. The last advantage differentiates from carbon burning operations which must take place at relatively high temperatures, e.g., 400° C. or higher in oxygen and, generally, requires removal of the catalyst from the reactor, an expensive, time-consuming operation in commercial reactors.

Ruthenium may promote hydrogenolysis and the intimate association of ruthenium with cobalt might allow carbon deposits on the catalyst to be gasified via hydrogenolysis as opposed to carbon gasification via combustion with oxygen in cobalt catalysts other than those having the structure disclosed herein.

DESCRIPTION OF THE DRAWINGS

FIG. 1 shows that the onset of reduction begins at a lower temperature with a calcined cobalt-ruthenium catalyst. A cobalt-ruthenium catalyst not prepared in accordance with the procedures of this invention and wherein the cobalt and ruthenium are not intimately associated, reacts similarly as a cobalt only catalyst.

FIG. 2 follows the behavior of the catalysts heated from room temperature to 500° C. in 1:1 $H_2/CO$ following a prereduction. The large gain of weight between 300° and 500° C. results from the growth of carbon. When the cobalt and ruthenium are in intimate contact, the growth of carbon is suppressed.

The cobalt only catalyst behaves similarly to a cobalt-ruthenium catalyst wherein the cobalt and ruthenium are not in intimate contact, i.e., not precalcined.

Figure 3:
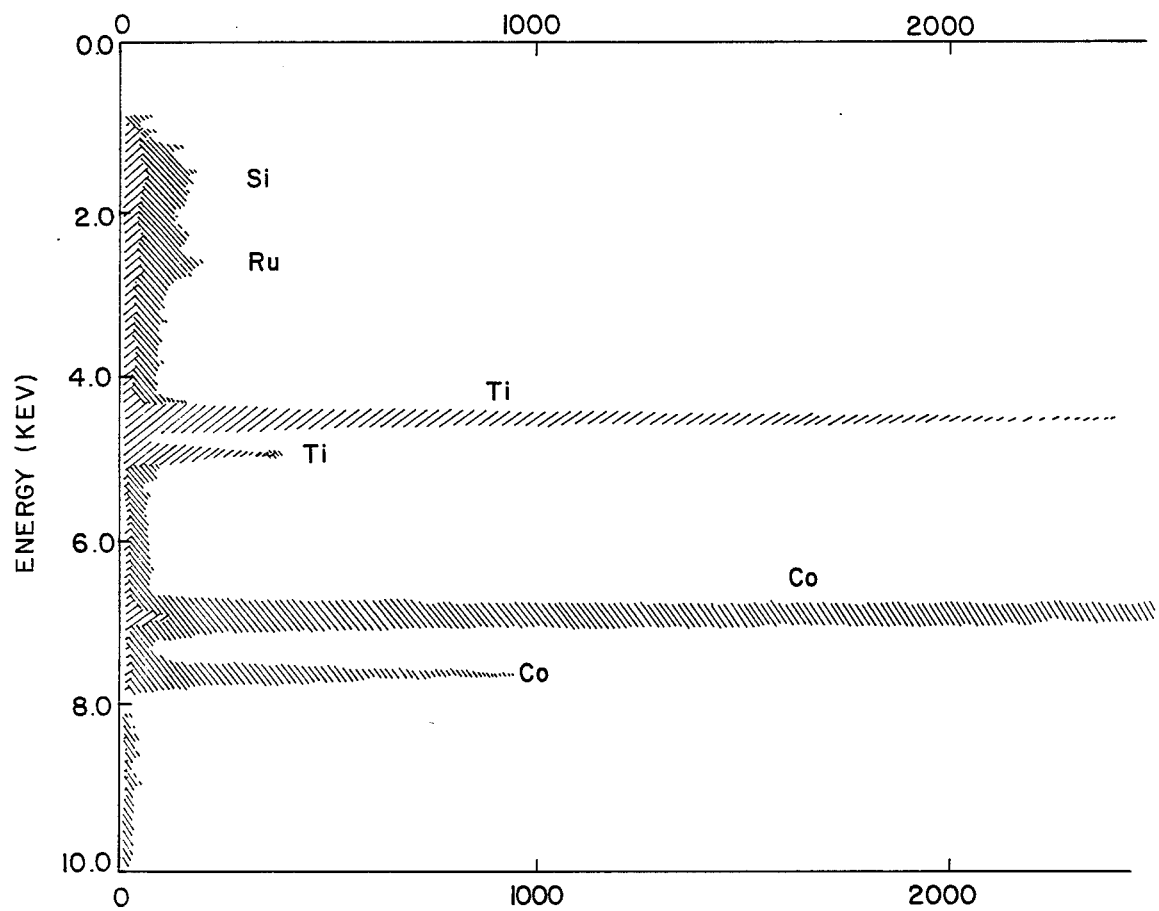
Figure 4:
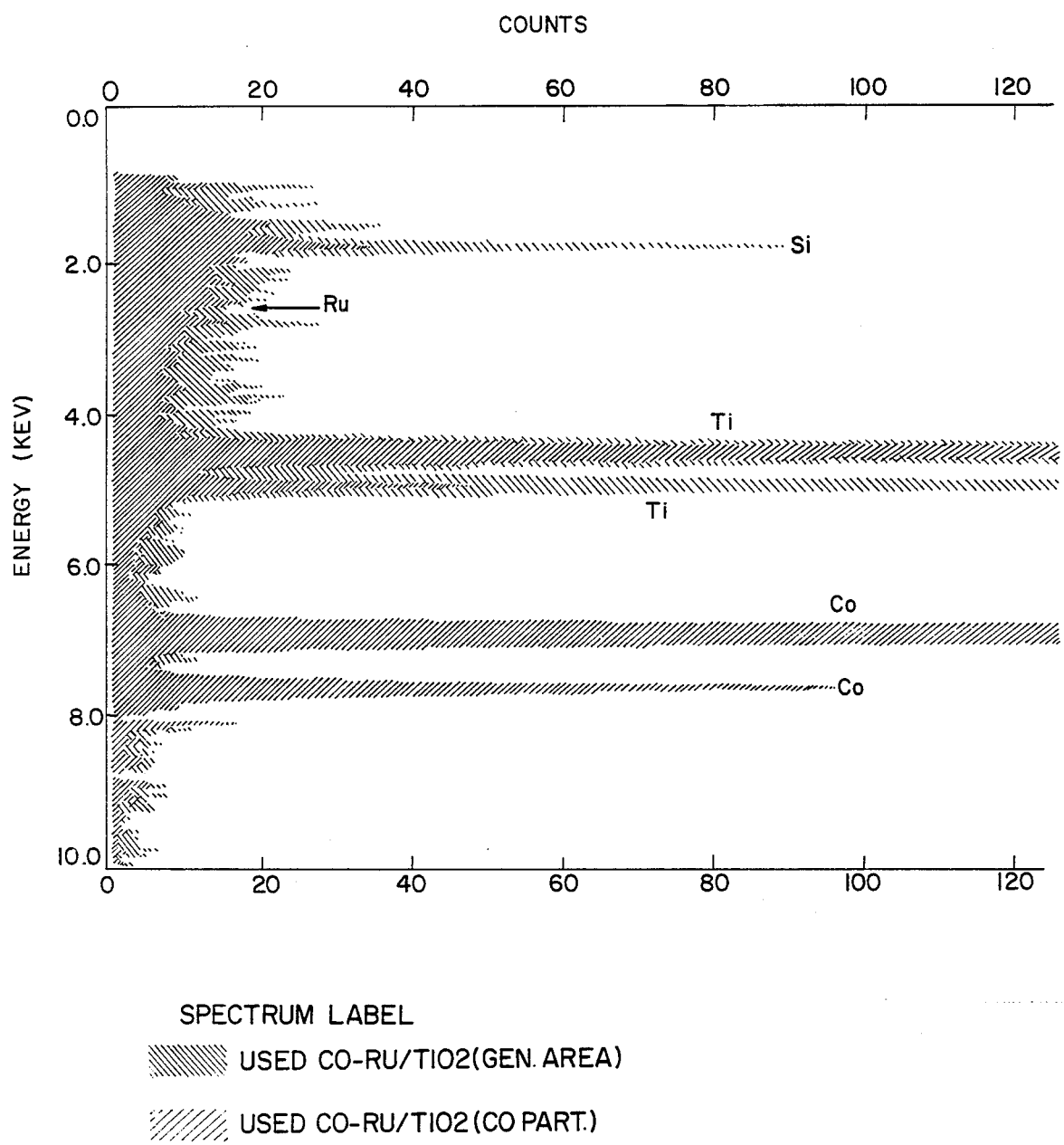

FIGS. 3 and 4 show the results of traces of a cobalt-ruthenium catalyst prepared in accordance with this invention and developed from analysis with a high resolution transmission electron microscope with scanning transmission and energy dispersive x-ray analysis capabilities. FIGS. 3 and 4 show energy dispersive x-ray traces (EDX) of calcined and uncalcined $CoRu/TiO_2$ catalysts. The figures show that following the calcination and rereduction treatment the ruthenium has concentrated in the area of the cobalt particle rather than remaining uniformly present throughout the support as it appears on the uncalcined, reduced catalyst.

DETAILED DESCRIPTION

In general, the hydrocarbon synthesis reaction is carried out at conditions that are known in the art. The $H_2$:CO ratio is at least about 0.5 and up to about 10, preferably 0.5 to 4.0, and more preferably about 1.0 to 2.5. The gas hourly space velocity can range from about 100 v/hr/v to about 5000 v/hr/v, preferably from about 300 v/hr/v to about 1500 v/hr/v and reaction temperatures may range from about 160° C. to about 300° C., preferably about 190° C. to 260° C., while pressures are above about 80 psig, preferably about 80 to 600 psig, more preferably about 140 to 400 psig. Hydrocarbon synthesis results in the formation of hydrocarbons of carbon number range $C_5$ to about $C_{40}$ or higher. Preferably, the synthesized hydrocarbons are primarily or almost completely paraffins.

The catalyst, cobalt and ruthenium on titania, contains about 5 to 25 wt.% cobalt, preferably 10 to 15 wt.% cobalt and about 0.03 to 0.30% ruthenium, preferably about 0.1 to 0.2 wt.% ruthenium. The atomic ratio of cobalt to ruthenium is about 10 to 400, preferably about 100 to 200.

The catalytic metals are supported on titania which may be used alone or with other inorganic refractory materials. Preferably, the support material is titania and more preferably the titania has a rutile:anatase ratio of at least about 2:3 as determined by x-ray diffraction (ASTM D3720-78), preferably about 2:3 to about 100:1 or higher, more preferably about 4:1 to 100:1 or higher, e.g., 100% rutile. The surface area of the support is, generally, less than about 50 $m^2$/gm (BET).

Preparation of the catalyst is not believed to be a critical step insofar as deposition of the catalytic metals on the support is concerned. The intimate contact between the cobalt and the ruthenium is accomplished by subjecting the composition to an oxygen treatment subsequent to reduction of both of the metals. Consequently, the metals can be deposited (i.e., impregnated) on the support either in serial fashion—with the cobalt being deposited either before or after depositing the ruthenium—or by co-impregnating the metals onto the carrier. In the case of serial impregnation, the carrier is preferably dried and the metal reduced prior to impregnation of the second metal after which drying and reduction is effected again and prior to the treatment of the catalyst with an oxygen containing gas.

Preferably, the catalyst is prepared by depositing the cobalt, drying the catalyst, reducing the cobalt, depositing the ruthenium, also followed by drying and reduction, and to effect the intimate contact of the cobalt and ruthenium exposure to an oxygen containing gas, and a final reduction.

Thus, the catalyst can be prepared by incipient wetness impregnation of the titania support with an aqueous solution of a cobalt salt, e.g., nitrate, acetate, acetyl acetonate or the like, the nitrate being preferred. The impregnated support is then dried and reduced in a reducing gas, such as hydrogen. Ruthenium is added to the reduced cobalt on titania catalyst using a ruthenium salt, e.g., ruthenium nitrate, chloride, acetylacetonate, carbonyl, etc. The catalyst is again dried and again reduced in a reducing gas, such as hydrogen. Intimate association of the cobalt and ruthenium is accomplished by treating the reduced cobalt-ruthenium on titania catalyst with an oxidizing gas, e.g., air or a dilute oxygen stream such as 20% oxygen in helium at elevated temperatures sufficient to oxidize the cobalt and ruthenium, for example above about 250° C., preferably 250° to 300° C.; but not in excess of about 600° C. because of excessive oxide sintering. Upon reduction, the cobalt and ruthenium are intimately associated, that is, atoms of each are much closer together than would otherwise be the case and are believed to be present in the same crystallite. Cobalt and ruthenium oxides in the bulk form a cobalt-ruthenium single phase mixed metal oxide. The available evidence suggests a likely bimetallic cluster formation of Co and Ru on the titania support. Reduction is effected in hydrogen at about 400° C. but can take place at temperatures ranging from about 200° to 500° C. Reduction of the catalyst is generally easier, that is, occurs at lower temperatures, relative to a catalyst containing only cobalt without ruthenium.

In virtually any catalyst process, catalyst activity decreases as run length increases due to a variety of factors: deposition of coke or carbon on the catalyst as a result of cracking, hydrogenolysis, or polymerization, buildup of poisons in the feed such as sulfur or nitrogen compounds, etc. In hydrocarbon synthesis reactions carbon tends to build up or grow (by complex polymerization mechanisms) on the surface of the catalyst, thereby shielding the catalytic metals from the reactants. Activity decreases and at some pre-set level of activity (as defined by conversion or selectivity or both), the process becomes sufficiently uneconomical to continue and the catalyst is either replaced or regenerated. In either case, downtime results and in the former, significantly increased catalyst costs are incurred.

Catalyst regeneration is desirable, particularly where regeneration can be accomplished without removing the catalyst from the reactor. Using the catalyst of this invention, regeneration can be effected by discontinuing the flow of carbon monoxide (and continuing the flow of hydrogen if the gases are supplied separately) to the reactor or discontinuing the flow of synthesis gas (where synthesis gas is the feed as produced, for example, by methane reforming or partial oxidation of methane) and flowing hydrogen to the reactor. After regeneration with hydrogen, synthesis gas flow to the reactor is resumed and the hydrocarbon synthesis reaction continued. The regeneration process may be conducted at intervals to return the catalyst to initial activity levels. Thus, a cyclical operation involving hydrocarbon synthesis and regeneration may be repeated.

The temperature in the reaction zone during hydrogen regeneration is preferably at or slightly above hydrocarbon synthesis reaction temperatures and pressures can be the same, as well; although neither temperature nor pressure are critical to the regeneration which is effected by the hydrogenolysis characteristics of the ruthenium bound intimately with the cobalt. In the case where the ruthenium is not intimately bound with the cobalt, i.e., not in the same crystallite, hydrogenolysis of the carbon deposited on the catalyst may have little or no effect on carbon deposited on the cobalt sites. Where the ruthenium and cobalt are in intimate association, ruthenium-promoted hydrogenolysis affects the carbon deposited on the particular crystallite and both cobalt and ruthenium sites are regenerated, that is, freed of carbon deposits. It is only necessary that the conditions be conducive to hydrogenolysis promoted by ruthenium and carried out for a time sufficient to regenerate the catalyst. Preferably, temperatures range from about 150° C. to about 300° C., more preferably about 190° C. to 260° C. and the hydrogen flow is continued until regeneration is effected, about 8 hours, preferably at least about 10 hours.

Regeneration results in the recovery of at least about 90%, preferably 95%, more preferably at least 100% of initial activity as measured by cobalt-time yields and is accompanied by $C_{5}+$ yields greater than initially and $CH_4$ yields below initial yields. By "initial" we mean after the catalyst has stabilized, usually about 24 hours after startup.

EXAMPLE 1

Preparation and Evaluation of Supported Cobalt Catalysts

Four cobalt-containing catalysts were prepared, three with titania as a support and one with silica. For catalyst A, 50 grams of Degussa P-25 titania was calcined at 560° C. for 4 hours. X-ray diffraction showed that the titania contained 70% rutile and 30% anatase; the BET-measured surface area was 30 $m^2$/gm. 35 gms of cobalt nitrate hexahydrate $Co(NO_3)_2.6H_2O$ (Alfa, Puratronic Grade) were dissolved in 20 cc of doubly-distilled deionized water. Half of the solution was impregnated by incipient wetness onto the titania. After the sample was dried at 100° C. the remaining solution was impregnated onto the titania and the catalyst was dried at 100° for 16 hours. Following calcination in air at 400° C. for 4 hours, the catalyst was placed in a tube furnace at 400° C. in a hydrogen flow of 2000 cc $H_2$/cc cat/hr for a period of 16 hours. After this reduction, He was introduced for 2 hours and then a 1% stream of oxygen was added to the helium to passivate the catalyst and allow its removal into the ambient environment. Subsequent cobalt chemical analysis showed the cobalt content to be 11.6%. Catalyst A therefore consists of 11.6% $Co/TiO_2$ and is designated as $Co/TiO_2$ in the following examples.

For catalyst B, 20 grams of 11.6% $Co/TiO_2$ (a portion of catalyst A) were selected. 1.02 grams of ruthenium nitrate (hydrate) were dissolved in 102 cc of acetone. 20 grams of catalyst A were slurried into this solution and the solvent was allowed to evaporate while being stirred. The catalyst was dried, reduced, and passivated as described above.

To prepare Catalyst C, 10 grams of B were heated in 20% $O_2$/80% He at 300° C. for 4 hrs., rereduced in $H_2$ and passivated as described above. The cobalt and ruthenium contents in catalysts B and C were 11.6 and 0.14% respectively, corresponding to an atomic Co/Ru ratio of 160. The catalysts B and C are designated as $CoRu/TiO_2$ and $CoRu(c)TiO_2$ in the following examples.

Catalyst D, containing cobalt on silica, was prepared for comparison purposes. 30 grams of Davison 62 silica were calcined at 600° C. for 4 hours. 50 grams of cobalt nitrate hexahydrate were dissolved in 40 cc of water. The solution was impregnated onto the silica in four steps with intermediate dryings at 100° C. The catalyst was then dried, reduced and passivated as described above. Chemical analyses indicated that the Co content was 23%. This catalyst is designated as $Co/SiO_2$ in the following examples.

EXAMPLE 2

Effect of Ru Promoter and Calcination at Low Pressures

5–10 $cm^3$ of catalysts A, B, C, and D from Example 1 were run in a single pass fixed bed reactor of ⅜ inch outer diameter. Hydrogen, carbon monoxide and nitrogen were obtained as a preblended mixture with 61±2% $H_2$, 31±2% CO and 7±1% $N_2$. The feed mixture was passed over a $Pd/Al_2O_3$ catalyst (Deoxo, Johnson Mathey), an activated charcoal sieve, and a 13X molecular sieve trap, to remove water, oxygen, and Ni and Fe carbonyls. Gas flows were controlled by Brooks mass flow controllers. Pressure was maintained with backpressure regulators. Temperature was held isothermal to within ±2 degrees by use of a Thermac temperature controller. Products were analyzed by capillary and packed column gas chromatography, using $N_2$ as an internal standard. $C_{20}$–$C_{200}$ molecular weight distributions were obtained by gas chromatography and gel permeation chromatography. Pretreated and passivated catalysts were rereduced in flowing hydrogen (200–400 GHSV) at 400° C. for 4 hours in the hydrocarbon synthesis reactor before Fischer-Tropsch experiments.

Table I compares the Fischer-Tropsch synthesis behavior of $Co/TiO_2$ (Catalyst A) with the bimetallic $CoRu/TiO_2$ both directly reduced (Catalyst B) and calcined/rereduced (Catalyst C) as well as the comparative $Co/SiO_2$ catalyst (Catalyst D). Hydrocarbon synthesis rates are reported as cobalt-normalized rates, i.e., cobalt time-yields, defined as the moles of CO converted per hour per g-atom Co in the catalyst or as site-normalized rates (site-time yields) defined as the molecules of CO converted per hour per surface cobalt atom in the catalyst. The number of surface cobalt atoms is determined from $H_2$ chemisorption measurements. Hydrocarbon selectivities are reported on a carbon atom basis as the percentage of the converted CO which appears as a given product.

At 560 kPa the addition of Ru to $Co/TiO_2$ (Co/Ru gm atom ratio 160) increases time yields more than threefold while decreasing $CH_4$ selectivity from 10.1% to 7.9%. Calcination of the bimetallic catalyst has a minor effect on selectivity, but it increases time yields by an additional 50%. $Co/SiO_2$ shows similar selectivities with about 50% higher time yield than $Co/TiO_2$, because of the proportionately higher cobalt loading.

EXAMPLE 3

Catalysts A, B, and C were also compared at higher pressure, 2050 kPa, in the same reactor. Table II lists the results. At these conditions calcination of the bimetallic $Co-Ru/TiO_2$ significantly improves performance. Time yields double with the addition of Ru to the $Co/TiO_2$ but improve an additional 70% following calcination. In addition, $CH_4$ selectivity decreases from 7.5 to 5.0% and the $C_5+$ fraction increases from 86 to 91% following calcination and reduction.

EXAMPLE 4

Catalysts A, B, and C from Example 1 were run in a fixed bed reactor as described in Example 2 at 200° C.

and 560 kPa. During the run the conversions were varied between 5 and 70% by adjusting the space velocity between 200 and 3000 v/v/hr. Table III shows the $CH_4$ and $C_5+$ selectivities as a function of CO conversion. For all three catalysts, the $CH_4$ selectivity decreases and the $C_5+$ selectivity increases with increasing conversion. At all conversion levels the methane yields are lower and $C_5+$ yields higher for the Ru promoted catalysts. At all levels of conversion the calcination of the $CoRu/TiO_2$ catalyst decreases $CH_4$ and increases $C_5+$ selectivities.

TABLE I

Fischer-Tropsch Activities and Selectivities at 560 kPa

| Catalyst | GHSV | CO Conversion % | $CH_4$ (% Wt) | $CH_5+$ (% Wt) | Cobalt-Time Yield ($h^{-1}$) | Space-Time Yield ($h^{-1}$) |
|---|---|---|---|---|---|---|
| $Co/SiO_2$ (D) | 450 | 28.9 | 8.4 | 78.8 | 130 | 1.0 |
| $Co/TiO_2$ (A) | 300 | 27.7 | 10.1 | 79.4 | 83 | 0.6 |
| $CoRu/TiO_2$ (B) | 1200 | 26.0 | 7.9 | 85.7 | 310 | 2.0 |
| $CoRu/TiO_2$ (C) (Calcined) | 1800 | 25.3 | 7.5 | 86.7 | 455 | 2.9 |

[200° C., $H_2/CO$ = 2.05, 560 kPa]

TABLE II

Fischer-Tropsch Activities and Selectivities at 2050 kPa

| Catalyst | GHSV | CO Conversion % | $CH_4$ (% Wt) | $CH_5+$ (% Wt) | Cobalt-Time Yield ($h^{-1}$) | Space-Time Yield ($h^{-1}$) |
|---|---|---|---|---|---|---|
| $Co/TiO_2$ (A) | 450 | 48.7 | 7.0 | 85.0 | 220 | 1.4 |
| $CoRu/TiO_2$ (B) | 800 | 50.7 | 7.5 | 86.1 | 405 | 2.6 |
| $CoRu/TiO_2$ (C) (Calcined) | 1200 | 61.0 | 5.0 | 91.4 | 730 | 4.7 |

[200° C., $H_2/CO$ = 2.05, 2050 kPa]

TABLE III

Fischer-Tropsch Activities and Selectivities as a Function of Conversion

| Catalyst | $Co/SiO_2$ (D) | | $Co/TiO_2$ (A) | | $CoRu/TiO_2$ (B) | | $CoRu/TiO_2$ (C) | |
|---|---|---|---|---|---|---|---|---|
| Cobalt Time Yield | 1 | 1 | 0.6 | 0.6 | 2.0 | 2.0 | 2.9 | 2.8 |
| CO Conversion | 7 | 65 | 4 | 50 | 5 | 64 | 5 | 68 |
| $CH_4$ Selectivity | 9.5 | 7.4 | 12 | 9.3 | 8.6 | 6.8 | 7.8 | 6.5 |
| $C_5+$ Selectivity | 75 | 82 | 77.3 | 80.2 | 84.9 | 87.3 | 85.3 | 87.8 |

Conditions: 200° C., 560 kPa, $H_2/CO$ = 2/1, conversion varied by changing space velocity

EXAMPLE 5

Catalysts A, B and C from Example 1 were run for periods of 10–30 days. During those time periods catalyst activity declines. Table IV shows the effect of hydrogen treatments on reactivating these catalysts.

TABLE IV

Regeneration of Co Catalysts by $H_2$ Treatments

| | Cobalt-Time Yield ($h^{-1}$) | $CH_4$ (Wt %) | $C_5+$ (Wt %) |
|---|---|---|---|
| (A) $Co/TiO_2$ (4) | | | |
| Initial | 0.6 | 8.9 | 80.1 |
| Before $H_2$ treatment (2) | 0.5 | 9.5 | 81 |
| After $H_2$ treatment (1) | 0.5 | 9.5 | 80.5 |
| (B) $CoRu/TiO_2$ (3) | | | |
| Initial | 2.6 | 7.0 | 86 |
| Before $H_2$ treatment (2) | 2.0 | 8.2 | 84 |
| After $H_2$ treatment (1) | 2.6 | 6.5 | 87 |
| (C) $CoRu/TiO_2$ (3) (calcined) | | | |
| Initial | 4.5 | 5.5 | 91.0 |
| Before $H_2$ treatment (2) | 3.9 | 6.4 | 88.8 |
| After $H_2$ treatment (1) | 4.8 | 4.9 | 91.5 |

(1) 24–48 hr. after $H_2$
(2) $H_2$ treatment at 200–230° C. for 16 hr, 100 kPa
(3) Conditions, 50–60% CO conversion, 2060 kPa, 200° C., $H_2/CO$ = 2/1
(4) Conditions, 20% CO conversion 560 kPa, $200^2$C, $H_2/CO$ = 2/1

For $Co/TiO_2$, the CO conversion and $CH_4$ and $C_5+$ selectivities do not respond appreciably to $H_2$ treatments, whereas the Ru containing catalysts respond to the hydrogen treatment by regaining their original activity and selectivity. For the calcined catalyst (C), all results are superior to the results for the uncalcined catalyst (B).

EXAMPLE 6

The calcined Co-Ru/$TiO_2$ catalyst (catalyst C) was run at two temperatures at a constant pressure of 2060 kPa. Space velocities were adjusted to keep conversion levels comparable. Table V presents the results.

TABLE V

Effect of Temperature on Performance of CoRu(c)/$TiO_2$ (C)

| Temperatures T/°C. | 184.8 | 200.0 |
|---|---|---|
| GHSV | 600 | 1200 |
| CO Conversion (%) | 57.2 | 59.1 |
| Cobalt-Time Yield ($h^{-1}$) | 2.2 | 4.6 |
| $E_{CO}$/Kcal $mol^1$ | | 21 |
| Carbon Selectivity (%) | 3.4 | 5.4 |

TABLE V-continued

Effect of Temperature on Performance of CoRu(c)/TiO$_2$ (C)

| CH$_4$ | | |
|---|---|---|
| E$_{CH_4}$(Kcal mol$^{-1}$) | 34 | |
| C$_2$ | 0.40 | 0.43 |
| C$_3$ | 1.59 | 1.68 |
| C$_4$ | 1.66 | 1.77 |
| C$_5$+ | 92.9 | 90.7 |

[CoRu(C)/TiO$_2$ 2060 kPa, H$_2$/CO = 2.05]
0.14% Ru, 11.6% Co

At higher temperatures selectivity to lighter products increases. The calcined Ru promoted catalyst run at 15° C. lower temperature has cobalt time yields comparable to the unpromoted Co/TiO$_2$ and much higher C$_5$+ selectivity. Therefore, improved selectivities (less CH$_4$ and more C$_5$+) are obtained at comparable metal yields.

EXAMPLE 7

Catalysts A and C were compared at different temperatures. Table VI lists the results.

TABLE VI

| | CoRu(C)/TiO$_2$ (C) | Co/TiO$_2$ (A) |
|---|---|---|
| Temp. | 185 | 200 |
| Co Time Yield (h$^{-1}$) | 2.2 | 1.4 |
| C$_5$+ | 93 | 85 |
| CH$_4$ | 3.4 | 7 |

The data show that at similar cobalt time yields, the CoRu(c)/TiO$_2$ catalyst produces substantially more C$_5$+ and less CH$_4$ than the Co/TiO$_2$ catalyst, the calcined catalyst being more active and more selective to valuable products.

EXAMPLE 8

Figure 1:
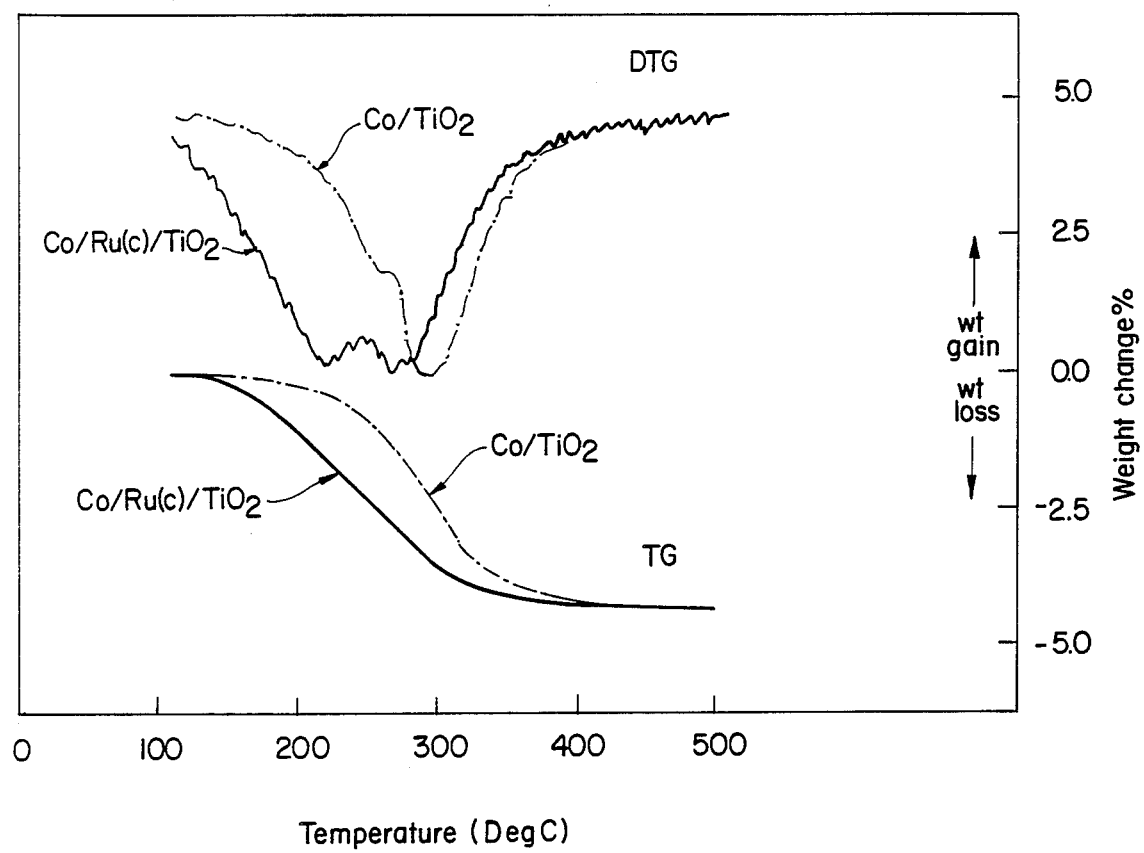
FIG. 1 shows the effect of intimate association of cobalt and ruthenium on reduction temperatures as opposed to cobalt alone. The TG curve monitor's weight changes as the supported cobalt oxide is reduced in hydrogen from room temperature to 500° C. at 6 deg/min. The DTG plots the rate of weight change with time as a function of temperature.
Figure 2:
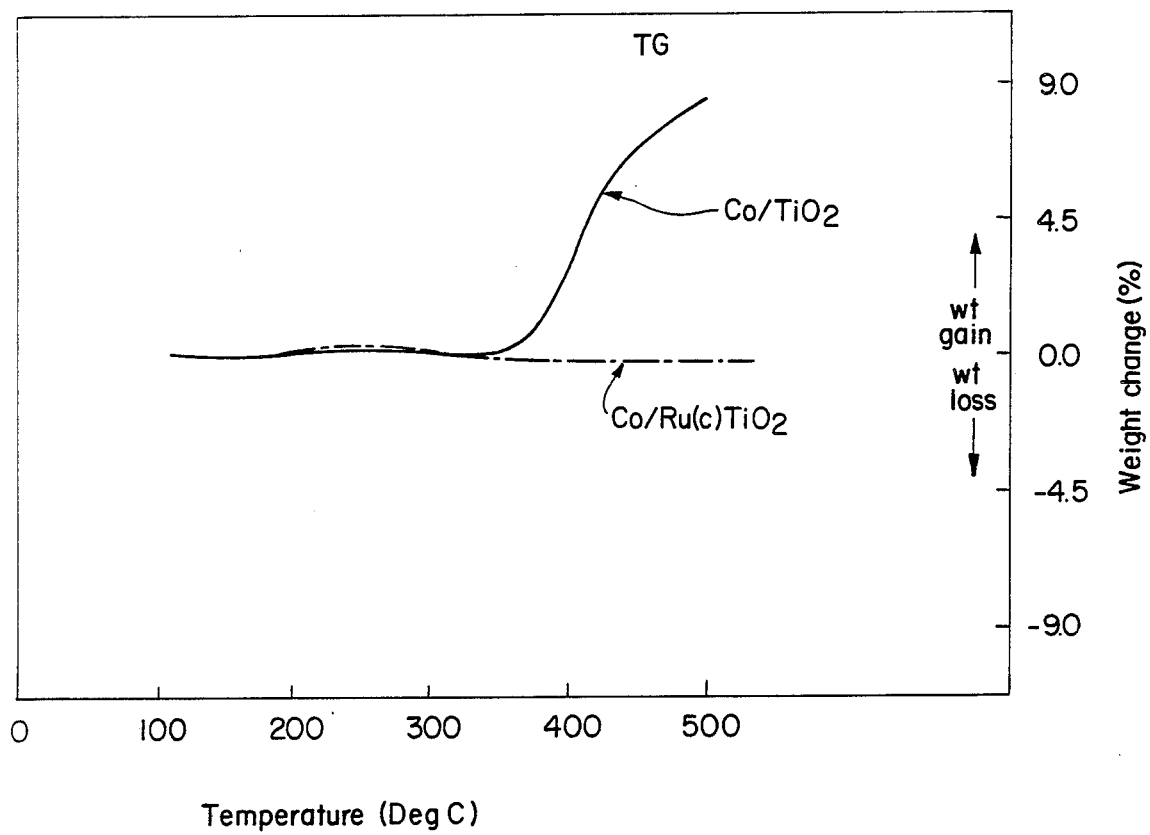
FIG. 2 shows the effect of cobalt and ruthenium being in intimate contact on catalyst carburization, i.e., the tendency of carbon to grow on active sites of the catalyst as opposed to a cobalt only catalyst.

The Co/TiO$_2$ and CoRu(c)/TiO$_2$ catalysts from Example 1 were treated under hydrogen in a thermalgravimetric analyzer (TGA). The samples were heated from room temperature to 500° C. at 6 deg/min. The TG curve monitors weight changes as the cobalt oxide is reduced to cobalt metal. The DTG plots the rate of weight change with time as a function of temperature. FIG. 1 shows the onset of reduction begins at a lower temperature with the CoRu(c)/TiO$_2$ catalyst. This indicates that the cobalt and ruthenium have come into intimate association on the catalyst. FIG. 2 shows the behavior of the Co/TiO$_2$ and CoRu(c)/TiO$_2$ catalysts in a 1:1 H$_2$/CO mixture following reduction. The calcined CoRu/TiO$_2$ catalyst does not grow carbon at temperatures where the noncalcined CoRu/TiO$_2$ or Co/TiO$_2$ do. Therefore, a combination of increased cobalt oxide reducibility and inhibited catalyst poisoning by carbon are believed to account for the increased number of active sites observed on calcined CoRu/TiO$_2$ catalysts.

EXAMPLE 9

CoRu/TiO$_2$ (catalyst B) and CoRu(c)/TiO$_2$ (catalyst C) were run under Fischer-Tropsch conditions for 700 hours, including two hydrogen regeneration treatments. Electron microscopy studies of these catalysts were conducted using a Phillips EM-420ST high-resolution transmission electron microscope with scanning transmission and energy dispersive x-ray analysis capabilities. Under the conditions used in this study, the instrument had a resolution of better than 0.25 nm. The catalyst samples were ground using a mullite mortar and pestle and was ultrasonically dispersed in butyl alcohol. A drop of the suspension was then air dried on a carbon film.

Identification of the elements in the catalyst was made using the adjunct energy dispersive x-ray (EDX) analyzer. Using the EDX system, particles as small as 1 nm were analyzed. With these catalysts and with a 1 nm beam for analysis, the x-ray spatial resolution was approximately 2.5 nm. Detectability limits for the elements in question were about 0.3–0.4 weight percent in the volume analyzed. FIG. 3 shows the results.

The morphology of the cobalt particles on titania is similar on both monometallic and bimetallic catalysts. Cobalt is dispersed on the titania as slightly elliptical particles 20–50 nm in size. EDX analysis of these particles suggests that ruthenium is present with the cobalt in the same crystallite after calcination and reduction treatments. FIG. 3 shows that following the calcination and rereduction treatment the ruthenium has concentrated in the area of the cobalt particles so that ruthenium above detectability limits was not observed on the titania, but was only in the cobalt particles. (In the uncalcined CoRu/TiO$_2$ (FIG. 4), ruthenium was below detection limits on the support and in the cobalt particles, indicating that Ru was not preferentially concentrated, but remained uniformly present.)

What is claimed is:

1. A hydrocarbon synthesis catalyst prepared by a process comprising impregnating a refractory support comprising titania with solutions of catalytically active amounts of cobalt and ruthenium salts, drying the impregnated support, reducing the cobalt and ruthenium, treating the reduced metals with an oxygen containing stream at conditions sufficient to form oxides of cobalt and oxides of ruthenium and reducing the cobalt and ruthenium oxides.

2. The catalyst of claim 1 wherein cobalt is present in amounts ranging from about 5 to 25 wt.% of the catalyst and the atomic ratio of cobalt to ruthenium is about 10/1 to 400/1.

3. The catalyst of claim 2 wherein the titania support has a rutile to anatase ratio of at least about 2:3.

4. The catalyst of claim 3 wherein the surface area of the support is less than about 50 m$^2$/gm (BET).

5. A process for preparing a hydrocarbon synthesis catalyst which comprises impregnating a refractory support comprising titania with solutions of catalytically active amounts of cobalt and ruthenium salts, drying the impregnated support, reducing the cobalt and ruthenium, treating the reduced metal with an oxygen containing stream at conditions sufficient to form oxides of cobalt and oxides of ruthenium, and reducing the cobalt and ruthenium oxides.

6. The process of claim 5 wherein the cobalt and ruthenium are co-impregnated onto the support.

7. The process of claim 5 wherein the cobalt is first impregnated onto the support, dried and reduced in hydrogen and then the ruthenium is impregnated onto the support, dried and reduced in hydrogen.

8. The process of claim 7 wherein the reduced metals are treated with an oxygen containing stream at a temperature above about 250° C. for a period sufficient to form cobalt oxide and ruthenium oxide or a bimetallic cobalt-ruthenium oxide.

9. The process of claim 8 wherein the cobalt and ruthenium oxides are reduced in the presence of hydrogen at temperatures ranging from about 200° C. to about 500° C.

10. The process of claim 5 wherein the cobalt and ruthenium salts are aqueous.

* * * * *